United States Patent [19]

Schmidt et al.

[11] 4,146,384
[45] Mar. 27, 1979

[54] TETRAHYDROFURAN-ETHER COMPOUNDS AND HERBICIDAL COMPOSITIONS

[75] Inventors: Thomas Schmidt; Wilfried Draber, both of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 878,546

[22] Filed: Feb. 16, 1978

[30] Foreign Application Priority Data

Mar. 3, 1977 [DE] Fed. Rep. of Germany ....... 2709144

[51] Int. Cl.² ............... A01N 9/28; C07D 307/20
[52] U.S. Cl. ............... 71/88; 260/340.5 R; 260/347.2; 260/347.4; 260/347.8
[58] Field of Search ............... 260/347.8, 347.4, 347.2, 260/340.5 R; 71/88

[56] References Cited

U.S. PATENT DOCUMENTS

| 2,421,569 | 6/1947 | LaForge et al. | 260/340.5 R X |
| 3,046,191 | 7/1962 | Beroza | 260/340.5 R X |
| 3,318,916 | 5/1967 | Leonard | 260/347.4 X |

OTHER PUBLICATIONS

Eliel et al., Chemical Abstracts, vol. 63, (1965), 5585f.

Glukhovtsev et al., Chemical Abstracts, vol. 70, (1969), 87407e.

*Primary Examiner*—Richard Raymond
*Attorney, Agent, or Firm*—Sprung, Felfe, Horn, Lynch & Kramer

[57] ABSTRACT

New tetrahydrofuran-ether compounds of the formula

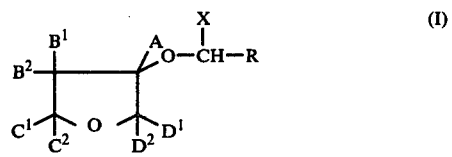

in which
A is hydrogen, alkyl, alkenyl, alkynyl, cycloalkyl, phenyl, or substituted phenyl,
$B^1$, $B^2$, $C^1$, $C^2$, $D^1$ and $D^2$, which are selected independently of one another, each represent hydrogen, alkyl, haloalkyl, alkoxyalkyl, phenyl, or substituted phenyl,
R is aryl or substituted aryl; and
X is hydrogen, alkyl, alkenyl, alkynyl, haloalkyl, phenyl, or substituted phenyl;

exhibit powerful herbicidal, especially selectively herbicidal, properties and are particularly useful as grass herbicides.

25 Claims, No Drawings

TETRAHYDROFURAN-ETHER COMPOUNDS AND HERBICIDAL COMPOSITIONS

The present invention relates to certain new tetrahydrofuran-ether compounds, to herbicidal compositions containing them, and to their use as herbicides, especially as selective herbicides.

It has been disclosed that certain chloroacetanilides, for example 2-ethyl-6-methyl-N-(1'-methyl-2'-methoxyethyl)chloroacetanilide, can be used as herbicides, especially for combating grass-like weeds (see German Offenlegungsschrift (German Published Specification) No. 2,328,340). However, the selectivity of these compounds is not always satisfactory.

The present invention now provides, as new compounds, the tetrahydrofuran-ether derivatives of the general formula

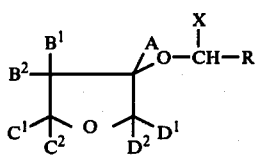

in which
A is hydrogen, alkyl, alkenyl, alkynyl, cycloalkyl, phenyl, or substituted phenyl,
$B^1$, $B^2$, $C^1$, $C^2$, $D^1$ and $D^2$, which are selected independently of one another, each represent hydrogen, alkyl, haloalkyl, alkoxyalkyl, phenyl, or substituted phenyl,
R is aryl or substituted aryl; and
X is hydrogen, alkyl, haloalkyl, alkenyl, alkynyl, phenyl, or substituted phenyl.

These tetrahydrofuran-ether derivaties exhibit powerful herbicidal, especially selectively herbicidal, properties.

Surprisingly, the tetrahydrofuran-ether derivatives according to the invention are distinctly superior, in their herbicidal action, to the previously known agents for combating grasses, such as, for example, 2-ethyl-6-methyl-N-(1'-methyl-2'-methoxyethyl)-chloroacetanilide, and furthermore exhibit an excellent selectivity in important crop plants. The active compounds according to the invention thus represent an important enrichment of herbicidal agents, especially of grass herbicides.

Preferably, A represents hydrogen, straight-chain or branched alkyl with 1 to 6 carbon atoms, cycloalkyl with 3–6 carbon atoms, alkenyl or alkynyl each with 2 to 4 carbon atoms or phenyl, which is optionally substituted by halogen, alkyl or alkoxy each with 1 or 2 carbon atoms or halogenoalkyl with up to 2 carbon atoms and up to 3 halogen atoms (which halogen atoms are selected independently, especially from fluorine and chlorine atoms);

$B^1$, $B^2$, $C^1$, $C^2$, $D^1$ and $D^2$, which are selected independently of one another, each represent hydrogen, straight-chain or branched alkyl with 1 to 6 carbon atoms, alkoxyalkyl with 1 or 2 carbon atoms in each alkyl part, halogenoalkyl with up to 2 carbon atoms and up to 3 halogen atoms (which halogen atoms are selected independently, especially from fluorine, chlorine and bromine atoms) or phenyl which is optionally substituted by halogen, alkyl or alkoxy each with 1 or 2 carbon atoms or halogenoalkyl with up to 2 carbon atoms and up to 3 halogen atoms (which halogen atoms are selected independently, especially from fluorine and chlorine atoms);

R represents optionally substituted aryl with 6 to 10 carbon atoms (especially phenyl or naphthyl) which can carry one or more substituents selected, independently, from halogen (especially fluorine, chlorine or bromine), alkyl and alkoxy each with 1 to 4 carbon atoms, halogenoalkyl, halogenoalkoxy and halogenoalkylthio each with up to 4 carbon atoms and up to 5 halogen atoms (especially with up to 2 carbon atoms and up to 3 halogen atoms, which halogen atoms are selected, independently, from fluorine, chlorine and bromine), phenyl, phenoxy and phenoxycarbonyl [which are each optionally substituted by halogen (especially fluorine, chlorine or bromine), alkyl or alkoxy each with 1 or 2 carbon atoms or halogenoalkyl with up to 2 carbon atoms and up to 3 halogen atoms (which halogen atoms are selected, independently, from fluorine and chlorine)], alkoxycarbonyl with 1 to 4 carbon atoms in the alkyl part, the methylenedioxo group, or the trimethylene, tetramethylene or pentamethylene radical; and X represents hydrogen, straight-chain or branched alkyl with 1 to 4 carbon atoms, alkenyl or alkynyl each with 2 to 4 carbon atoms, halogenoalkyl with up to 2 carbon atoms and up to 3 halogen atoms (which halogen atoms are selected independently from fluorine and chlorine) and phenyl which is optionally substituted by halogen, alkyl or alkoxy each with 1 or 2 carbon atoms or halogenoalkyl with up to 2 carbon atoms and up to 3 halogen atoms (which halogen atoms are selected independently, especially from fluorine and chlorine atoms).

The invention also provides a process for the preparation of a tetrahydrofuran-ether derivative of the formula (I) in which (a) an alcoholate of a 3-hydroxytetrahydrofuran derivative, of the general formula

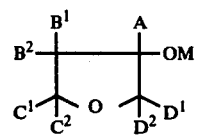

in which
A, $B^1$, $B^2$, $C^1$, $C^2$, $D^1$ and $D^2$ have the above-mentioned meanings and
M represents an alkali metal or an equivalent of an alkaline earth metal, preferably sodium, potassium or an equivalent of calcium or magnesium, is reacted with a compound of the general formula

in which
R and X have the above-mentioned meanings and
Y represents halogen, especially chlorine or bromine, the mesylate radical or the tosylate radical, in the presence of a diluent, or (b) a butanediol of the general formula

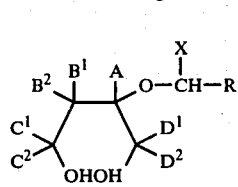

in which

A, $B^1$, $B^2$, $C^1$, $C^2$, $D^1$, $D^2$, R and X have the above-mentioned meanings, is heated in the presence of an acid catalyst and optionally in the presence of a diluent.

If the sodium alcoholate of 3-hydroxytetrahydrofuran and 2-fluorobenzyl bromide are used as starting materials in process variant (a), the course of the reaction can be represented by the following equation:

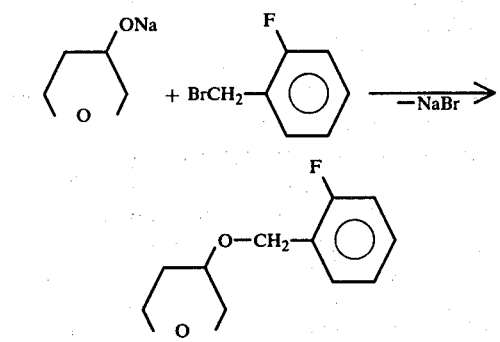

If 2-(2-fluorobenzyloxy)-butane-1,4-diol is used as the starting material and p-toluenesulphonic acid as the catalyst in process variant (b), the course of the reaction can be represented by the following equation:

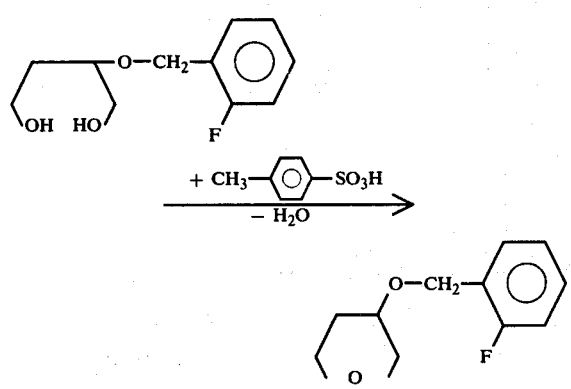

The alcoholates of the formula (II) are known or can be prepared in accordance with known methods. For example, they are obtained by reacting the corresponding 3-hydroxytetrahydrofuran derivatives with suitable strong bases, such as, for example, alkali metal or alkaline earth metal amides, hydrides or hydroxides, in an inert solvent. The 3-hydroxytetrahydrofuran derivatives mentioned are also known or can be prepared in accordance with known methods (see, inter alia, Houben-Weyl, Methoden der organischen Chemie (Methods of Organic Chemistry), volume 6/3, page 519 et seq. (1965) and the literature cited there).

The following may be mentioned as examples of the 3-hydroxytetrahydrofuran derivatives from which the alcoholates of the formula (II), to be used according to the invention as starting materials, are derived: 3-hydroxy-tetrahydrofuran, 3-hydroxy-2,2,5,5-tetramethyl-tetrahydrofuran, 3-hydroxy-2,5-dimethyl-tetrahydrofuran, 3-hydroxy-2-methyl-tetrahydrofuran, 3-hydroxy-3-phenyl-tetrahydrofuran, 3-hydroxy-3-ethyl-tetrahydrofuran, 3-hydroxy-3-ethynyl-tetrahydrofuran and 3-hydroxy-2-phenyl-tetrahydrofuran.

The starting materials of the formula (III) are generally known compounds of organic chemistry. As examples there may be mentioned: benzyl chloride, benzyl bromide, benzylmesylate, benzyltosylate, 2-fluorobenzyl bromide, 3-fluorobenzyl bromide, 4-fluorobenzyl bromide, 2-chlorobenzyl chloride, 3-chlorobenzyl chloride, 4-chlorobenzyl chloride, 2-bromobenzyl chloride, 3-bromobenzyl chloride, 4-bromobenzyl chloride, 2-methylbenzyl chloride, 3-methylbenzyl chloride, 4-methylbenzyl chloride, 2-methoxybenzyl chloride, 3-methoxybenzyl chloride, 4-methoxybenzyl chloride, 2-trifluoromethylbenzyl chloride, 3-trifluoromethylbenzyl chloride, 4-trifluoromethylbenzyl chloide, 4-phenylbenzyl chloride, 2,6-difluorobenzyl chloride, 2,6-dichlorobenzyl chloride, 2,4-dichlorobenzyl chloride, 3,4-dichlorobenzyl chloride, 2,5-dichlorobenzyl chloride, 2,6-dimethylbenzyl chloride, 2,4-dimethylbenzyl bromide, 3,4-dimethylbenzyl chloride, 2,3-dimethylbenzyl chloride, 3,4-methylenedioxybenzyl chloride, 2,6-chlorofluorobenzyl chloride, 2-fluoro-5-chlorobenzyl bromide, 2-fluoro-4-chlorobenzyl bromide, 3-chloro-4-fluorobenzyl bromide, 3,4-tetramethylenebenzyl chloride, 2-methyl-6-chlorobenzyl chloride, 2-methyl-6-fluorobenzyl chloride, 2-fluoro-3-methylbenzyl chloride, 2-fluoro-4-methylbenzyl chloride, 2-fluoro-5-methylbenzyl chloride, 2-methyl-3-chlorobenzyl chloride, 2-methyl-4-chlorobenzyl chloride, 2-methyl-5-chlorobenzyl chloride, 2,4,5-trichlorobenzyl bromide, 2,4,6-trichlorobenzyl bromide, diphenylmethyl bromide, 1-bromo-1-phenylethane, 1-bromo-1-(2-fluorophenyl)-ethane and 1-bromo-1-(2-methylphenyl)-ethane.

The butanediols of the formula (IV) are known or can be prepared in accordance with known methods. They are obtained, for example, by preparing the ether from a malic acid ester and a benzyl halide in the presence of silver oxide and then reducing it with a complex metal hydride in the presence of an inert solvent, such as, for example, ether, at 0°-50° C.

The following may be mentioned as examples of starting materials of the formula (IV): 2-benzyloxy-butane-1,4-diol, 2-(2-fluorobenzyloxy)-butane-1,4-diol, 2-(2-fluorobenzyloxy)-3,3-dimethyl-butane-1,4-diol, 2-(2-fluorobenzyloxy)-2,3-dimethyl-butane-1,4-diol and 2-(2-methylbenzyloxy)-butane-1,4-diol.

For the reaction according to the invention, in accordance with the process variant (a), preferred diluents are inert organic solvents, especially ethers, such as diethyl ether, tetrahydrofuran or dioxan, aromatic hydrocarbons, such as benzene or toluene, and in a few cases also chlorinated hydrocarbons, such as chloroform, methylene chloride or carbon tetrachloride.

In process variant (a), the reaction temperatures can be varied within a substantial range. In general, the reaction is carried out at from 0° to 120° C., preferably at from 20° to 100° C.

In carrying out process variant (a) according to the invention, equimolar amounts are preferably used. However, it is also possible to employ the alcoholate of the formula (II) or the compound of the formula (III) in an excess of up to 1 mol. To isolate the end product, water is added to the reaction mixture, and the organic phase is separated off and worked up and purified in the usual manner. In a few cases, the end product can also be distilled from the reaction mixture directly after the solvent.

An advantageous procedure is to start from a 3-hydroxytetrahydrofuran derivative, convert it, in a suitable inert solvent, by means of an alkali metal hydride or alkali metal amide, into the alkali metal alcoholate of the formula (II), and react the latter immediately, without isolation, with a compound of the formula (III), thus obtaining the compound according to the invention, of the formula (I), in one process step. In this embodiment, the compound of the formula (III) can also be added to the reaction mixture before preparing the alcoholate.

According to another preferred embodiment, the preparation of the alcoholate of the formula (II), as well as the reaction in accordance with process variant (a), is effected in a two-phase system, such as, for example, aqueous sodium hydroxide solution or potassium hydroxide solution/toluene or methylene chloride, with addition of a phase transfer catalyst, such as, for example, and ammonium compound.

For the reaction according to the invention, in accordance with process variant (b), possible diluents are again inert organic solvents such as ethers, aromatic hydrocarbons or chlorinated hydrocarbons. The reaction in accordance with process variant (b) is, however, preferably carried out without a diluent or solvent.

The reaction in accordance with process variant (b) is carried out in the presence of an acid catalyst. All inorganic and organic acid catalysts which can usually be employed may be used, especially organic acids, such as p-toluenesulphonic acid, inorganic acids, such as hydrochloric acid and sulphuric acid, and metal halides, such as aluminium chloride.

The reaction temperatures in process variant (b) can be varied within a substantial range. In general, the reaction is carried out at from 80° to 250° C., preferably from 100° to 220° C.

To isolate the end products, in the case of process variant (b), the reaction mixture is distilled in vacuo and the water is then separated off in the usual manner.

The compounds of the formula (I) can, where relevant, be present as the various geometrical isomers, which can be produced in different ratios. Furthermore, they are in each case present as optical isomers. All the isomers are intended to be covered by formula (I).

The following may be mentioned as particularly active compounds according to the invention: 3-benzyloxy-5-methyl-tetrahydrofuran, 3-(2-fluorobenzyloxy)-5-methyl-tetrahydrofuran, 3-(2-chlorobenzyloxy)-5-methyl-tetrahydrofuran, 3-(2-methylbenzyloxy)-5-methyl-tetrahydrofuran, 3-(2,6-difluorobenzyloxy)-5-methyl-tetrahydrofuran, 3-(2,6-dimethylbenzyloxy)-5-methyltetrahydrofuran, 3-(2-fluoro-6-chlorobenzyloxy)-5-methyltetrahydrofuran, 3-(2-fluoro-6-methylbenzyloxy)-5-methyltetrahydrofuran, 3-(2-chloro-6-methylbenzyloxy)-5-methyltetrahydrofuran, 3-benzyloxy-5-phenyl-tetrahydrofuran, 3-(2-fluorobenzyloxy)-5-phenyl-tetrahydrofuran, 3-(2-chlorobenzyloxy)-5-phenyl-tetrahydrofuran, 3-(2-methylbenzyloxy)-5-phenyl-tetrahydrofuran, 3-(2,6-difluorobenzyloxy)-5-phenyl-tetrahydrofuran, 3-(2,6-dimethylbenzyloxy)-5-phenyl-tetrahydrofuran, 3-(2-fluoro-6-chlorobenzyloxy)-5-phenyl-tetrahydrofuran, 3-(2-fluoro-6-methylbenzyloxy)-5-phenyl-tetrahyrofuran, 3-(2-chloro-6-methylbenzyloxy)-5-phenyl-tetrahydrofuran, 3-benzyloxy-5-chloromethyl-tetrahydrofuran, 3-(2-fluorobenzyloxy)-5-chloromethyl-tetrahydrofuran, 3-(2-chlorobenzyloxy)-5-chloromethyl-tetrahydrofuran, 3-(2-methylbenzyloxy)-5-chloromethyl-tetrahydrofuran, 3-(2,6-difluorobenzyloxy)-5-chloromethyl-tetrahydrofuran, 3-(2,6-dimethylbenzyloxy)-5-chloromethyl-tetrahydrofuran, 3-(2-fluoro-6-chlorobenzyloxy)-5-chloromethyl-tetrahydrofuran, 3-(2-fluoro-6-methylbenzyloxy)-5-chloromethyl-tetrahydrofuran, 3-(2-chloro-6-methylbenzyloxy)-5-chloromethyl-tetrahydrofuran, 3-benzyloxy-5-methoxymethyl-tetrahydrofuran, 3-(2-fluorobenzyloxy)-5-methoxymethyl-tetrahydrofuran, 3-(2-chlorobenzyloxy)-5-methoxymethyl-tetrahydrofuran, 3-(2-methylbenzyloxy)-5-methoxymethyl-tetrahydrofuran, 3-(2,6-difluorobenzyloxy)-5-methoxymethyl-tetrahydrofuran, 3-(2,6-dimethylbenzyloxy)-5-methoxymethyl-tetrahydrofuran, 3-(2-fluoro-6-chlorobenzyloxy)-5-methoxymethyl-tetrahydrofuran, 3-(2-fluoro-6-methylbenzyloxy)-5-methoxymethyl-tetrahydrofuran, 3-(2-chloro-6-methylbenzyloxy)-5-methoxymethyl-tetrahydrofuran, 3-(2,6-dichlorobenzyloxy)-5-methyl-tetrahydrofuran, 3-(2,6-dichlorobenzyloxy)-5-phenyl-tetrahydrofuran, 3-(2,6-dichlorobenzyloxy)-5-chloromethyl-tetrahydrofuran, 3-(2,6-dichlorobenzyloxy)-5-methoxymethyl-tetrahydrofuran, 3-benzyloxy-4,4-dimethyl-tetrahydrofuran, 3-(2-fluorobenzyloxy)-4,4-dimethyl-tetrahydrofuran, 3-(2-chlorobenzyloxy)-4,4-dimethyl-tetrahydrofuran, 3-(2-methylbenzyloxy)-4,4-dimethyl-tetrahydrofuran, 3-(2,6-dichlorobenzyloxy)-4,4-dimethyl-tetrahydrofuran, 3-benzyloxy-5,5-dimethyl-tetrahydrofuran, 3-(2-fluorobenzyloxy)-5,5-dimethyl-tetrahydrofuran, 3-(2-chlorobenzyloxy)-5,5-dimethyl-tetrahydrofuran, 3-(2-methylbenzyloxy)-5,5-dimethyl-tetrahydrofuran, 3-(2,6-dichlorobenzyloxy)-5,5-dimethyl-tetrahydrofuran, 3-benzyloxy-2,2-dimethyl-tetrahydrofuran, 3-(2-fluorobenzyloxy)-2,2-dimethyl-tetrahydrofuran, 3-(2-chlorobenzyloxy)-2,2-dimethyl-tetrahydrofuran, 3-(2-methylbenzyloxy)-2,2-dimethyl-tetrahydrofuran, 3-(2,6-dichlorobenzyloxy)-2,2-dimethyl-tetrahydrofuran, 3-benzyloxy-5-ethyl-tetrahydrofuran, 3-(2-fluorobenzyloxy)-5-ethyl-tetrahydrofuran, 3-(2-chlorobenzyloxy)-5-ethyl-tetrahydrofuran, 3-(2-methylbenzyloxy)-5-ethyl-tetrahydrofuran, and 3-(2,6-dichlorobenzyloxy)-5-ethyl-tetrahydrofuran, 3-benzyloxy-2,5-diethyl-tetrahydrofuran, 3-(2-fluorobenzyloxy)-2,5-diethyl-tetrahydrofuran, 3-(2-chlorobenzyloxy)-2,5-diethyl-tetrahydrofuran, 3-(2-methylbenzyloxy)-2,5-diethyl-tetrahydrofuran, 3-(2,6-dichlorobenzyloxy)-2,5-diethyl-tetrahydrofuran, 3-benzyloxy-2-trichlormethyl-tetrahydrofuran, 3-(2-fluorobenzyloxy)-2-trichlormethyl-tetrahydrofuran, 3-(2-chlorobenzyloxy)-2-trichlormethyl-tetrahydrofuran, 3-(2-methylbenzyloxy)-2-trichlormethyl-tetrahydrofuran, 3-(2,6-dichlorobenzyloxy)-b 2-trichlormethyl-tetrahydrofuran, 3-benzyloxy-5-trichlormethyl-tetrahydrofuran, 3-(2-fluorobenzyloxy)-5-trichlormethyl-tetrahydrofuran, 3-(2-chlorobenzyloxy)-5-trichlormethyl-tetrahydrofuran, 3-(2-methylbenzyloxy)-5-trichlormethyl-tetrahydrofuran, 3-(2,6-dichlorobenzyloxy)-5-trichlormethyl-tetrahydrofuran.

The active compounds according to the invention influence plant growth and can therefore be used as defoliants, desiceants, agents for destroying broad-leaved plants, germination inhibitors and, especially, as weed-killers. By "weeds" in the broadest sense there are meant plants growing in places where they are not desired. Whether the compounds according to the invention act as total herbicides or selective herbicides depends essentially on the amount used.

The active compounds according to the present invention may be used, for example, to combat the following plants: dicotyledon weeds such as mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), field cress (Rorippa), toothcup (Rotala), false pimpernel (Linderna), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea) and nightshade (Solanum); and monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera).

The active compounds according to the present invention may be used, for example, as selective herbicides in the following cultures:

dicotyledon cultures such as cotton (Gossypium), soya bean (Glycine), beet (Beta), carrot (Daucus), bean (Phaseolus), pea (Pisum), potato (Solanum), flax (Linum), sweet potato (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cucurbita); and monocotyledon cultures such as rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these plants or even to the indicated genera but also embraces other plants, in the same way.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the invention can advantageously be employed for the selective combating of weeds and especially of wild grasses in various cultures. Using the active compounds according to the invention it is possible - in contrast to the chloroacetanilides known as grass herbicides - successfully to combat the wild grasses *Avena fatua* or Alopecurus, which are difficult to combat, simultaneously with other harmful grasses, for example Digitaria, Echinochloa, Panicum or Setaria, in cultures such as sugarbeet, soya beans, beans, cotton, rape, groundnuts, species of vegetables, maize and rice.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention, as such or in their formulations, can be combined with other herbicidal active compounds to boost and supplement their spectrum of action, depending on the intended use; for this purpose, finished formulations or tank mixing may be employed.

The combinations of the active compounds according to the invention with 4-amino-3-methyl-6-phenyl-1,2,4-triazin-5(4H)-one (Metamitron) for beet cultures, 4-amino-6-tert.-butyl-3-methylthio-1,2,4-triazin-5(4H)-one (Metribuzin) for soya beans, tomatoes and potatoes and 2-chloro-4-ethyl-amino-6-isopropylamino-1,3,5-triazine (Atrazin) for maize and sorghum should be singled out particularly.

The formulations in general contain from 0.1 to 95 percent by weight of active compound, preferably from 0.5 to 90 percent by weight.

The active compounds can be used as such, as their formulations or as the use forms prepared therefrom, such as ready-to-use solutions, emulsions, suspensions, powders, pastes and granules. They may be used in the customary manner, for example by spraying, atomising, dusting, scattering and watering.

The amount of active compound used can vary within a fairly wide range. It depends essentially on the nature of the desired effect. In general, the amounts used are from 0.1 to 10 kg of active compound per ha, preferably from 0.2 to 5 kg/ha.

The active compounds according to the invention can be applied both before and after the emergence of the plants. Preferably, they are employed in the pre-emergence process. They can also be worked into the soil before sowing.

The active compounds according to the invention not only possess herbicidal properties but in addition also fungicidal and insecticidal activity.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The activity of the compounds of this invention is illustrated by the following biotest Example.

In this Example, the compounds according to the present invention are each identified by the number (given in brackets) of the corresponding preparative Example, which will be found later in this specification.

The known comparison compound is identified as follows:

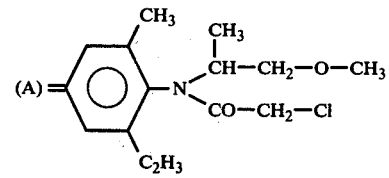

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

The active compounds, the amounts applied and the results can be seen from the table which follows:

Table A

| Active compound | Amount of active compound used, kg/ha | Sugar beet | Rape | Soya beans | Maize | Cotton | Echinochloa crusgalli | Avena fatua | Alopecurus myosuroides | Poa annua |
| --- | --- | --- | --- | --- | --- | --- | --- | --- | --- | --- |
| (A) | 1.5 | 10 | 30 | 30 | 20 | 0 | 90 | 65 | 50 | 70 |
|  | 1.0 | 10 | 10 | 20 | 10 | 0 | 90 | 65 | 40 | 50 |
| (16) | 1.5 | 0 | 0 | 0 | 0 | 0 | 100 | 100 | 100 | 100 |
|  | 1.0 | 0 | 0 | 0 | 0 | 0 | 100 | 90 | 100 | 90 |
| (1) | 1.5 | 0 | 0 | 0 | 0 | 0 | 100 | 100 | 100 | 100 |
|  | 1.0 | 0 | 0 | 0 | 0 | 0 | 100 | 90 | 100 | 100 |
| (7) | 1.5 | 0 | 0 | 0 | 0 | 0 | 100 | 100 | 100 | 100 |
|  | 1.0 | 0 | 0 | 0 | 0 | 0 | 100 | 100 | 100 | 100 |
| (50) | 1.5 | 0 | 0 | 0 | 80 | 0 | 100 | 100 | 100 | 100 |
|  | 1.0 | 0 | 0 | 0 | 40 | 0 | 100 | 90 | 90 | 100 |

Preparative Examples

Example 1

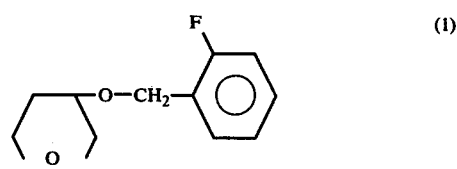

Process variant (a)

8.8 g (0.1 mole) of 3-hydroxy-tetrahydrofurane were added dropwise, whilst stirring, to a mixture of 2.8 g (0.12 mole) of sodium hydride (3.5 g of 80% strength sodium hydride in paraffin oil) in 100 ml of absolute dioxan at room temperature. The mixture was then heated for 30 minutes under reflux. After cooling to 50° C., 19 g (0.1 mol) of 2-fluorobenzyl bromide were added dropwise to the sodium salt thus obtained. The mixture was then heated for 3 hours under reflux and was allowed to cool to room temperature, 10 ml of methanol were added to destroy the excess sodium hydride, and the mixture was concentrated by distilling off the solvent in vacuo. The residue was taken up in 100 ml of water and extracted with methylene chloride. The organic phase was dried over sodium sulphate and concentrated. The residue was distilled in vacuo. 15.7 g (80% of theory) of 3-(2-fluorobenzyloxy)-tetrahydrofurane of boiling point 89° C./0.1 mm Hg were obtained.

Process variant (b)

0.1 g of p-toluenesulphonic acid was added to 4.26 g (0.02 mol) of 2-(2-fluorobenzyloxy)-butane-1,4-diol and the mixture was slowly heated to 200° C. under a water-pump vacuum. A mixture of water of reaction and 3-(2-fluorobenzyloxy)-tetrahydrofurane was obtained in the distillate. After fractional distillation, 3.8 g (97.5% of theory) of 3-(2-fluorobenzyloxy)-tetrahydrofurane of boiling point 140° C./14 mm Hg were obtained.

The compounds listed in Table 1 which follows were prepared analogously.

Table 1

(I)

| Example No. | A | $B^1$ | $B^2$ | $C^1$ | $C^2$ | $D^1$ | $D^2$ | X | R | Melting point (° C.) | Boiling point (° C./mm/Hg) |
|---|---|---|---|---|---|---|---|---|---|---|---|
| 2 | H | H | H | H | H | H | H | H |  | | 95/0.2 |
| 3 | H | H | H | H | H | H | H | H |  | | 105/0.2 |
| 4 | H | H | H | H | H | H | H | H |  | | 145/14 |
| 5 | H | H | H | H | H | H | H | H |  | | 90/0.08 |
| 6 | H | H | H | H | H | H | H | H |  | | 106/0.1 |
| 7 | H | H | H | H | H | H | H | H |  | | 80/0.06 |
| 8 | H | H | H | H | H | H | H | H |  | | 155/0.3 |
| 9 | H | H | H | H | H | H | H | H |  | | 80/0.2 |
| 10 | H | H | H | H | H | H | H | H |  | | 85/0.2 |
| 11 | H | H | H | H | H | H | H | H |  | | 120/0.1 |
| 12 | H | H | H | H | H | H | H | H |  | | 127/0.1 |
| 13 | H | H | H | $CH_3$ | $CH_3$ | $CH_3$ | $CH_3$ | H |  | | 87-89/0.1 |
| 14 | H | H | H | $CH_3$ | $CH_3$ | $CH_3$ | $CH_3$ | H | | | 109/0.1 |

Table 1-continued $$\begin{array}{c} \overset{X}{\underset{|}{}} \\ B^2 \overset{B^1}{\underset{|}{}} A \\ C^1 \overset{|}{\underset{C^2}{}} \overset{D^1}{\underset{D^2}{}} \end{array} \quad (I)$$

| Example No. | A | B¹ | B² | C¹ | C² | D¹ | D² | X | R | Melting point (°C.) | Boiling point (°C./mm/Hg) |
|---|---|---|---|---|---|---|---|---|---|---|---|
| 15 | H | H | H | H | H | H | H | H | 2,4-dichlorophenyl | | 150/0.3 |
| 16 | H | H | H | H | H | H | H | H | 2-methylphenyl | | 97/0.1 |
| 17 | H | H | H | H | H | H | H | H | 3,4-dimethylphenyl | | 114/0.1 |
| 18 | H | H | H | H | H | H | H | H | 3,4-methylenedioxyphenyl | | 121/0.1 |
| 19 | H | H | H | H | H | H | H | H | 4-methoxyphenyl | | 104/0.1 |
| 20 | H | H | H | H | H | H | H | H | 4-phenoxyphenyl | | 163/0.1 |
| 21 | H | H | H | H | H | H | H | H | 3,4,5-trichlorophenyl | | 135/0.1 |
| 22 | H | H | H | H | H | H | H | H | 2,3,5,6-tetrachloro-4-methylphenyl | 50 | |
| 23 | H | H | H | H | H | H | H | H | 3-methoxyphenyl | | 111/0.015 |
| 24 | H | H | H | H | H | H | H | H | 2,4,6-trichlorophenyl | | 125/0.1 |
| 25 | H | H | H | H | H | H | H | H | 5-chloro-3,4-methylenedioxyphenyl | | 158/1.5 |
| 26 | H | H | H | H | H | H | H | H | 3-chloro-4-trifluoromethoxyphenyl | | 114/0.1 |
| 27 | H | H | H | H | H | H | H | H | 4-fluorophenyl | | 104/0.1 |
| 28 | H | H | H | H | H | H | H | H | 4-trifluoromethoxyphenyl | | 99/0.1 |
| 29 | H | H | H | H | H | H | H | H | 2-chloro-4-trifluoromethylphenyl | | 127/0.1 |

Table 1-continued $$\underset{\underset{O}{C^1}\underset{C^2}{\diagdown}\underset{}{\diagup}\underset{D^2}{\overset{D^1}{\diagdown}}}{\overset{\overset{X}{|}}{\underset{B^2}{B^1}\underset{}{\overset{A}{\diagdown}}\underset{}{\overset{}{O-CH-R}}}} \quad (I)$$

| Example No. | A | B¹ | B² | C¹ | C² | D¹ | D² | X | R | Melting point (°C.) | Boiling point (°C./mm/Hg) |
|---|---|---|---|---|---|---|---|---|---|---|---|
| 30 | H | H | H | H | H | H | H | H | 2-Cl-3-CF₃-phenyl | | 112/0.1 |
| 31 | H | H | H | H | H | H | H | H | 2-CF₃-phenyl | | 95/0.1 |
| 32 | H | H | H | H | H | H | H | H | 4-CF₃-phenyl | | 97/0.1 |
| 33 | H | H | H | H | H | H | H | H | 2-CF₃-phenyl (with 2-CH₃) | | 97/0.1 |
| 34 | H | H | H | H | H | H | H | H | 4-SCF₃-phenyl | | 112/0.1 |
| 35 | H | H | H | H | H | H | H | H | 4-SCF₂Cl-phenyl | | 114/0.1 |
| 36 | H | H | H | H | H | H | H | phenyl | phenyl | | 122/0.1 |
| 37 | H | H | H | H | H | H | H | H | 2-Br-phenyl | | 104/0.1 |
| 38 | H | H | H | H | H | H | H | H | 2-CH₃-phenyl | | 96/0.1 ('S'-form) |
| 39 | H | H | H | H | H | H | H | H | 3-Cl-4-F-phenyl | | 91/0.09 |
| 40 | H | H | H | H | H | H | H | H | 2-Cl-3-F-phenyl | | 90/0.09 |
| 41 | H | H | H | H | H | H | H | H | 2-F-4-Cl-phenyl | | 94/0.1 |
| 42 | H | H | H | H | H | H | H | H | 2-F-4-Cl-phenyl | | 98/0.15 |
| 43 | H | H | H | H | H | H | H | H | 2-F-phenyl | | 140/15 ('S'-Form) |
| 44 | H | H | H | H | H | H | H | H | 4-phenyl-phenyl | | 162/0.05 |
| 45 | H | H | H | CH₃ | CH₃ | CH₃ | CH₃ | H | 2-F-phenyl | | 80/0.1 |
| 46 | H | H | H | H | H | H | CH₃ | H | phenyl | | 88/0.1 |
| 47 | H | H | H | H | H | H | CH₃ | H | 2-F-phenyl | | 85/0.1 |
| 48 | H | H | H | H | H | H | CH₃ | H | 2-CH₃-phenyl | | 91/0.05 |
| 49 | H | H | H | H | CH₃ | H | CH₃ | H | phenyl | | 80/0.1 |

Table 1-continued $$\begin{matrix} & & & & X \\ B^2 & B^1 & A & | \\ & & & O-CH-R \\ C^1 & & D^1 & \\ C^2 & & D^2 & \\ & O & \end{matrix} \quad (I)$$

| Example No. | A | B¹ | B² | C¹ | C² | D¹ | D² | X | R | Melting point (°C.) | Boiling point (°C./mm/Hg) |
|---|---|---|---|---|---|---|---|---|---|---|---|
| 50 | H | H | H | H | CH₃ | H | CH₃ | H |  (F) | | 80/0.1 |
| 51 | H | H | H | H | CH₃ | H | CH₃ | H |  (CH₃) | | 92/0.15 |
| 52 | C₂H₅ | H | H | H | H | H | H | H |  (F) | | Oil |
| 53 | ⟨○⟩ | H | H | H | H | H | H | H |  (F) | | 145/0.15 |
| 54 | ⟨○⟩ | H | H | H | H | H | H | H |  (CH₃) | | Oil |
| 55 | —C≡CH | H | H | H | H | H | H | H |  (F) | | Oil |
| 56 | —C≡CH | H | H | H | H | H | H | H |  (CH₃) | | Oil |
| 57 | H | H | H | H | H | H | H | H |  (F, F) | | 78/0.1 |
| 58 | H | H | H | CH₃ | H | CH₃ | H | H |  (Cl) | | 98/0.2 |
| 59 | H | C₂H₅ | H | H | H | H | H | H |  (F) | | 125/1.5 |
| 60 | H | H | H | H | H | CH₃ | CH₃ | H |  (F) | | 113/0.8 |
| 61 | H | CH₃ | CH₃ | H | H | H | H | H |  (F) | | 121/0.2 |
| 62 | H | CH₃ | CH₃ | H | H | CH₃ | CH₃ | H |  (F) | | 106/0.4 |
| 63 | H | H | H | H | H | C₂H₅ | C₂H₅ | H |  (F) | | 115/0.4 |
| 64 | H | H | H | H | H | C₂H₅ | C₂H₅ | H |  (CH₃) | | 116/0.2 |
| 65 | H | H | H | H | H | H | H | H |  (C₃H₇-i) | | 112/.07 |

Preparation of starting materials of the formula (IV)

EXAMPLE 1a

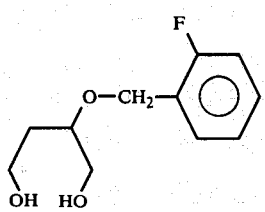

27 g (0.1 mol) of 2-(2-fluorobenzyloxy)-butane-1,4-dicarboxylic acid dimethyl ester were added dropwise, at 10° C., to a dispersion of 4.5 g of lithium aluminium hydride in 100 ml of absolute ether. After completion of the addition, the mixture was heated for 1 hour under reflux, and was cooled and hydrolysed with 35 ml of ice-water. After decanting the ether phase, the residue was repeatedly digested with ethanol. The combined organic phases were freed from the solvent and the residue was taken up in chloroform and chromatographed on a short silica gel column. The eluate was freed from the solvent and the residue was distilled. 7.5 g (35.5% of theory) of 2-(2-fluorobenzyloxy)-butane-1,4-diol of boiling point 155° C./0.5 mm Hg were obtained.

Preparation of the intermediate

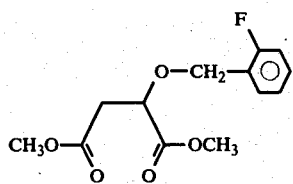

46.4 g (0.2 mol) of silver oxide were added in portions, with constant stirring, to a mixture of 16.2 g (0.1 mol) of malic acid dimethyl ester and 57 g (0.30 mol) of 2-fluorobenzyl bromide. An exothermic reaction started slowly, and the temperature rose to 80° C. After cooling, 200 ml of ether were added, the solid was filtered off, the filtrate was concentrated and the residue was distilled at 180° C. in a waterpump vacuum. 19.6 g (72.6% of theory) of 2-(2-fluorobenzyloxy)-butane-1,4-dicarboxylic acid dimethyl ester were obtained.

It will be understood that the specification and examples are illustrative, but not limitative of the present invention and that other embodiments within the spirit and scope of the invention will suggest themselves to those skilled in the art.

What is claimed is:

1. Tetrahydrofuran-ether compound of the formula

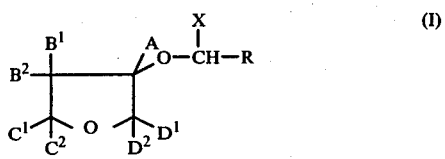

(I)

wherein

A is hydrogen, straight-chain or branched alkyl with 1 to 6 carbon atoms, cycloalkyl with 3-6 carbon atoms, alkenyl or alkynyl, each of up to 4 carbon atoms or phenyl optionally substituted by halogen, alkyl or alkoxy of 1 or 2 carbon atoms, or haloalkyl of up to 2 carbon atoms and up to 3 halogen atoms;

$B^1$, $B^2$, $C^1$, $C^2$, $D^1$ and $D^2$, which are selected independently of one another, each represent hydrogen, straight-chain or branched alkyl of 1 to 6 carbon atoms, alkoxyalkyl of 1 or 2 carbon atoms in each alkyl part, haloalkyl of up to 2 carbon atoms and up to 3 halogen atoms or phenyl optionally substituted by halogen, alkyl or alkoxy of 1 or 2 carbon atoms or haloalkyl of up to 2 carbon atoms and up to 3 halogen atoms;

R is optionally substituted aryl of 6 to 10 carbon atoms which can carry one or more substituents selected, independently, from halogen, alkyl and alkoxy, each with 1 to 4 carbon atoms, haloalkyl, haloalkoxy and haloalkylthio, each of up to 4 carbon atoms and up to 5 halogen atoms, phenyl, phenoxy and phenoxycarbonyl (which are each optionally substituted by halogen, alkyl or alkoxy, of 1 or 2 carbon atoms or haloalkyl of up to 2 carbon atoms and up to 3 halogen atoms), alkoxycarbonyl of 1 to 4 carbon atoms in the alkyl part, the methylenedioxo group, or the trimethylene, tetramethylene or pentamethylene radical; and X is hydrogen, straight-chain or branched alkyl of 1 to 4 carbon atoms, alkenyl or alkynyl of 2 to 4 carbon atoms, haloalkyl of up to 2 carbon atoms and up to 3 halogen atoms and phenyl which is optionally substituted by halogen, alkyl or alkoxy, of 1 or 2 carbon atoms or haloalkyl of up to 2 carbon atoms, and up to 3 halogen atoms.

2. Tetrahydrofuran-ether compound as claimed in claim 1 wherein A is hydrogen.

3. Tetrahydrofuran-ether compound as claimed in claim 1 wherein A is alkyl.

4. Tetrahydrofuran-ether compound as claimed in claim 1 wherein A is alkenyl or alkynyl.

5. Tetrahydrofuran-ether compound as claimed in claim 1 wherein A is cycloalkyl.

6. Tetrahydrofuran-ether compound as claimed in claim 1 wherein A is phenyl or substituted phenyl.

7. Tetrahydrofuran-ether compound as claimed in claim 1 wherein one of $B^1$, $B^2$, $C^1$, $C^2$, $D^1$ and $D^2$ is hydrogen.

8. Tetrahydrofuran-ether compound as claimed in claim 1 wherein one of $B^1$, $B^2$, $C^1$, $C^2$, $D^1$ and $D^2$ is alkyl, haloalkyl or alkoxyalkyl.

9. Tetrahydrofuran-ether compound as claimed in claim 1 wherein one of $B^1$, $B^2$, $C^1$, $C^2$, $D^1$ and $D^2$ is phenyl or substituted phenyl.

10. Tetrahydrofuran-ether compound as claimed in claim 1 wherein X is hydrogen.

11. Tetrahydrofuran-ether compound as claimed in claim 1 wherein X is alkyl or haloalkyl.

12. Tetrahydrofuran-ether compound as claimed in claim 1 wherein X is alkenyl or alkynyl.

13. Tetrahydrofuran-ether compound as claimed in claim 1 wherein X is phenyl or substituted phenyl.

14. Compounds as claimed in claim 1 wherein
R is optionally substituted aryl of 6 to 10 carbon atoms which can carry one or more substituents selected, independently, from halogen, alkyl and alkoxy, each with 1 to 4 carbon atoms, haloalkyl, haloalkoxy and haloalkylthio, each of up to 4 carbon atoms and up to 5 halogen atoms.

15. Tetrahydrofuran-ether compound as claimed in claim 1 of the formula

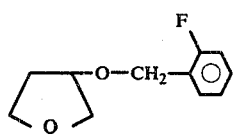

designated 3-(2-fluorobenzyloxy)-tetrahydrofuran.

16. Tetrahydrofuran-ether compound as claimed in claim 1 of the formula

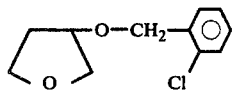

designated 3-(2-chlorobenzyloxy)-tetrahydrofuran.

17. Tetrahydrofuran-ether compound as claimed in claim 1 of the formula

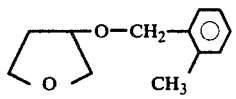

designated 3-(2-methylbenzyloxy)-tetrahydrofuran.

18. Tetrahydrofuran-ether compound as claimed in claim 1 of the formula

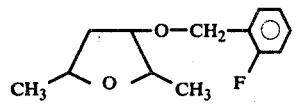

designated 3-(2-fluorobenzyloxy)-2,5-dimethyl-tetrahydrofuran.

19. Tetrahydrofuran-ether compound as claimed in claim 1 of the formula

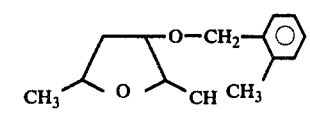

designated 3-(2-methylbenzyloxy)-2,5-dimethyl-tetrahydrofuran.

20. Tetrahydrofuran-ether compound as claimed in claim 1 of the formula

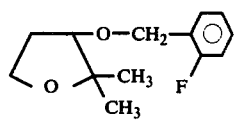

designated 3-(2-fluorobenzyloxy)2,2-dimethyl-tetrahydrofuran.

21. A herbicidal composition containing as active ingredient, herbicidally effective amount of a compound as claimed in claim 1 in admixture with a solid or liquefied gaseous diluent or liquid carrier containing a surface-active agent.

22. A composition as claimed in claim 21 containing from 0.1 to 95% of the active compound by weight.

23. A method of combating weeds which comprises applying to the weeds or their habitat, herbicidally effective amounts, a compound as claimed in claim 1.

24. A method as claimed in claim 23 wherein the active compound is applied to an area of agriculture in an amount of 0.1 to 10 kg per hectare.

25. A method as claimed in claim 24 wherein the active compound is applied to an area of agriculture in an amount of 0.2 to 5 kg per hectare.

* * * * *